United States Patent [19]

Sefton

[11] 4,353,888

[45] Oct. 12, 1982

[54] ENCAPSULATION OF LIVE ANIMAL CELLS

[76] Inventor: Michael V. Sefton, 21 Prince Charles Dr., Toronto, Ontario, Canada, M6A 2H1

[21] Appl. No.: 219,238

[22] Filed: Dec. 23, 1980

[51] Int. Cl.³ .......................... A61K 9/28; A61K 9/00
[52] U.S. Cl. ........................................ 424/25; 424/16; 424/31; 424/32; 435/2; 435/240
[58] Field of Search ............................ 435/241, 2, 240; 424/16, 31, 32, 19, 25

[56] References Cited

U.S. PATENT DOCUMENTS

| | | | |
|---|---|---|---|
| 3,717,551 | 2/1973 | Bizzini et al. | 435/241 |
| 4,036,693 | 7/1977 | Levine et al. | 435/241 |
| 4,184,922 | 1/1980 | Knazek et al. | 435/241 |

OTHER PUBLICATIONS

Chang et al.—Canadian J. of Physiol. & Pharmacol., vol. 44, (1966), pp. 115–128, (particularly 128).
Jack et al.—Advances in Biochem. Engineering, vol. 5, (1977), pp. 125–143, (particularly pp. 125–128).
Klein et al.—European Cong. on Biotechnology 1st Proceedings, (1978), pp. 142 and 145–148.

*Primary Examiner*—Sam Rosen
*Attorney, Agent, or Firm*—Fleit & Jacobson

[57] ABSTRACT

Viable mammalian cells are encapsulated in a polymeric membrane to form microencapsulated beads ready for introduction into a host body. The polymeric membrane allows passage therethrough of cell substrates and secretions, but prevents passage of larger molecules such as proteinaceous antibodies. In this way viable cells secreting essential products such as pancreatic islet cells secreting insulin can be transplanted into a host, and be protected against the immune reactions of the antibodies of the host which would otherwise reject the foreign cells. The cells are encapsulated from suspension in a non-solvent such as PPG, by addition thereto of a solution of a polymer (e.g. an acrylic/methacrylic acid esters copolymer) in dimethylsulfoxide. The polymer precipitates onto the cells to encapsulate them, and the supernatants are removed.

10 Claims, No Drawings

ENCAPSULATION OF LIVE ANIMAL CELLS

FIELD OF THE INVENTION

This invention relates to encapsulated biological cells and method of preparing microencapsulated cells in a form suitable for use in medical treatment.

BACKGROUND OF THE INVENTION

Many disorders in mammals and other living bodies are due to the lack of proper functioning natural cells of one type or another, with consequent lack of essential substances normally secreted by such cells. For example, diabetes is a disorder resulting from lack of properly functioning pancreatic islet cells, which normally produce and secrete insulin in response to glucose. Attempts to alleviate such conditions by transplantations of living, functioning animal cells, e.g. pancreatic islets, are limited by the immune rejection of these cells by the host body. Although the immune system can be artificially suppressed through chemotherapy and the transplant given an opportunity to succeed, this approach is not practical for large scale transplantations. The benefit to diabetics of such a pancreatic islet transplant would be enormous since not only would their reliance on exogenous insulin be reduced, but the insulin would be delivered in the natural control mode avoiding the periodic variation in glucose level associated with conventional therapy. It is believed that these variations are responsible for the degenerative complications of diabetes.

BRIEF DESCRIPTION OF THE PRIOR ART

As an alternative to chemotherapy, it has been possible to separate the "foreign" cells from the host by a membrane which selectively permits substrate, product and other biochemical agent exchange between the foreign cells and the host tissues but which prevents the higher molecular weight antibodies of the host from contacting the foreign cells. This has been achieved for pancreatic islets by separating rat islets from the host's blood (e.g. monkey) by a hollow fibre ultrafiltration membrane with a molecular weight "cut off" of 50,000 (see Sun et al., "Diabetes," 26, 1136 (1977)). This membrane which is preformed freely permits glucose and insulin transport but prevents the circulating antibodies (M.W. 150,000 typically) from crossing into the cell compartment. Unfortunately, a blood-material interface is introduced in this kind of device with the normal consequences of this interface (coagulation, thrombosis). The development of a different form of suitably protected living animal cells for transplantation into a host body is therefore desirable.

It is known to prepare small encapsulated beads containing soluble enzymes or whole microbial cells (see for example Chang et al., Cdn. J. Phys. Pharm., 44, 115 (1966); Klein et al., Proceed. I European Congress of Biotechnology (1978); Jack and Zajic, Adv. Biochem. Eng., 5, 125 (1977)). However, techniques described therein are not applicable to living animal cells, which are much more fragile.

SUMMARY OF THE INVENTION

The present invention provides small beads comprising a few viable cells, the cells being completely covered with polymer membrane formed in situ. The beads can be injected or otherwise introduced into the appropriate body compartment (such as the peritoneal cavity in the case of pancreatic islet cells). The thrombosis problem referred to above are avoided, since the injected beads are put into direct contact with live tissue, not with blood. The beads have a very large surface area. The membrane is a water insoluble polymeric material. The membrane and the reagents used in the encapsulation process are chosen to produce encapsulated but still viable cells, the membrane permitting passage therethrough of cell substrates, cell secretagogues, cell secretions and metabolic regulator, but inhibiting or preventing the passage of antibodies therethrough which might cause an immune reaction and rejection of the cells by the host body.

Thus according to the first aspect of the present invention, there is provided a process for preparing micro-encapsulated viable mammalian cells for introduction into host, living mammalian tissue, which comprises:

preparing an aqueous suspension of said viable mammalian cells;

bringing said aqueous suspension into contact with a solution of a biocompatible, water-insoluble polymer in a polar, non-toxic liquid optionally in the presence also of a water immiscible suspending medium, and forming a suspension having aqueous droplets containing said viable cells dispersed in a hydrophobic liquid medium;

causing the polymer to precipitate at the interface of the aqueous, cell-containing droplets and the hydrophobic phase so as to encapsulate some at least of the cells in said droplets with a membrane of said polymer;

separating the bulk of the hydrophobic medium and solvents from the encapsulated cellular material.

According to a second aspect of the invention, there is provided micro-encapsulated viable mammalian cells, said cells being in the form of discrete beads each containing a small number of said viable cells and each bead being encapsulated in a semi-permeable, water-insoluble, biocompatible polymeric membrane capable of allowing passage therethrough of cell substrate material and cell secretions, but effectively preventing passage therethrough of high molecular weight antibodies of a living organism.

DESCRIPTION OF THE PREFERRED EMBODIMENTS

In one preferred method of preparation of micro encapsulated cells according to the present invention, the cell aqueous suspension is dispersed, with agitation, in a suspending medium to form an emulsion with a continuous hydrophobic phase and a discontinuous aqueous phase comprising droplets each containing a small amount of viable cells. Then the polymer solution is added to the emulsion. Precipitation of the polymer can then be caused either by addition to the mixture of an additional non-solvent for the polymer, or substantially spontaneously due to the non-solvent character of the suspending medium. In such a procedure, the suspending medium should be a relatively high molecular weight, hydrophobic, non-toxic, non-cell-penetrating liquid. It should be miscible with the polymer solution, yet be preferably a non-solvent for the polymer. Preferred are mineral oils (hydrocarbon liquids with six or more carbon atoms per molecule), corn oils, and polypropylene glycol (PPG). Most preferred is PPG, partly on account of its well established utility in the preservation of viable cells for low temperature storage.

In an alternative procedure, the cell aqueous suspension may be added to the solution of the polymer in a suitable water immiscible solvent, to form a suspension thereof with discrete aqueous, cell-containing droplets therein. This suspension is then contacted with a suitable non-solvent for the polymer, to cause precipitation thereof at the water-solvent interface for micro encapsulation of the cells. The non-solvent for the polymer can be aqueous or hydrophobic, depending upon the solvent chosen for the polymer. Since the polymer solvent will normally be one of medium polarity, either type of non-solvent will normally be satisfactory.

A wide variety of polymers are available for use in the present invention. The polymer should be capable of ready solidification to form a membrane having the desired transport properties, and insoluble in water or saline at cellular pH. The desired transport properties, e.g. permeability in vivo, require that the polymer have a degree of polarity. The polymer membrane should contain 20–90% water at equilibrium. The polymer should be non-toxic in solution, and biocompatible in solid form, i.e. free from elutable contaminants, sterilizable, implantable without causing inflammatory or immune response, and either non-biodegradable or of controlled biodegradability. Examples of suitable polymers include polyacrylates and copolymers with acrylic acid, methacrylic acid and esters thereof, cellulose based polymers, copolymers containing acrylamides, N-vinyl pyrrolidone, styrene sulphonate, vinyl pyridine, vinyl alcohol, allyl alcohol and the like. A most preferred polymer is a copolymer of acrylic acid ester and methacrylic acid ester, with small amounts of quaternary ammonium groups. A specific example of such a preferred polymer, commercially available, is that known under the trade mark EUDRAGIT, manufactured by Rohm Pharma GmbH, of Darmstadt, W. Germany. This product is commonly used to coat dry tablets in slow release formulations.

The precise manner in which the polymer is precipitated onto the cells to form the membrane is not critical so long as a satisfactory encapsulation of a few cells to form encapsulated beads is achieved, without of course affecting the cells themselves. In a preferred method, the polymer solution in DMSO is added to the well stirred aqueous cell emulsion in PPG, with the result that the polymer precipitates at the interface of the water droplets to form a membrane shell about each droplet. In one alternative where, the cell emulsion is dispersed in the polymer solution, the polymer solution (containing dispersed cells) is added slowly to a polymer non-solvent to precipitate the polymer around the aqueous droplets. In another alternative, the polymer solution (containing dispersed cells) is added slowly to a polymer non-solvent immiscible with the polymer solvent, and then a second, miscible non-solvent is added slowly to this mixture to precipitate the polymer. Both the non-solvent and the solvent should of course be non-toxic, have low water solubility and high molecular weight. The non-solvent may be an isotonic aqueous solution at cellular pH, with or without surfactants (e.g. Tweens, Pluronics etc.) or other additives such as albumin. The non-solvent may be an organic liquid miscible with the polymer solvent, non-toxic, and hydrophobic and of high molecular weight (greater than 150) so that it does not penetrate the cells. Suitable examples are mineral oils, polyethers and polyether copolymers, natural and synthetic di- and tri-glycerides (e.g. corn oil, cotton seed oil etc.) and the like.

The choice of polymer solvent must be made with care. Since, in order to provide a membrane with suitable transport properties when encapsulating the cells a polar polymer must be used, the solvent liquid must also have a degree of polarity. At the same time, one must choose a polymer solvent having low specific toxicity, often an incompatible requirement. The best solvents for use in the present invention are either relatively high molecular weight, medium polarity, non-toxic solvents with no or negligible water solubility, such as dimethyl phthalate, dibutyl phthalate, and the like, or highly polar water soluble solvents such as dimethyl-sulfoxide and the like. In the first alternative method of encapsulating the cells outlined above, in which the polymer solution is added to a suspension of aqueous cells in, e.g. polypropylene glycol, dimethyl sulfoxide (DMSO) is the most preferred solvent, since this process can utilise a water miscible solvent such as DMSO, which also has other advantageous characteristics. Suitable alternative solvents for this process are highly polar, water soluble, and tolerated by the cells at least to a limited extent. In the second and third processes where the aqueous cell suspension is dispersed in the polymer solution, then the polymer solvent must be water immiscible. In this case, the solvent should have intermediate polarity, very low toxicity, and be one which does not penetrate the cells. It should have a water solubility less than about 0.5 gm per 100 milliliters. Solvents containing moderately hydrogen bonding functional groups (ester, ether, carbonyl or S=O groups, for example) as set out in the "Polymer Handbook," Bandrup and Immergut (Chapter 4), first edition, with a solubility parameter between 8 and 11, e.g. dialkyl phthalates and esters of dicarboxylic acids, are generally suitable. It is preferred to use solvents of molecular weight at least 150, otherwise the contact time of the solvent with the cells must be carefully reduced. Most preferred solvents for use in this process are dibutyl phthalate, diethylphthalate and dimethylphthalate.

After the polymer has been precipitated to encapsulate the cells, it is necessary to separate the cells from the liquid residues. This can done by centrifuging after a suitable period of time, followed by decanting off the residual solvent/non-solvent mixture and washing to remove residues thereof. Great care should be taken to rinse DMSO from the cells. The cells should be washed repeatedly in aqueous solution of DMSO of progressively lower concentrations to minimize the osmotic gradient. Alternatively, the DMSO may be removed by dialysis during or after encapsulation. When dialysis is conducted during encapsulation, the bottom of the encapsulation chamber may be formed as a membrane permeable to DMSO but impermeable to the hydrophobic non solvent, contacting a chamber containing saline. The encapsulation medium may be continuously dialysed against saline, in a separate unit, connected by a pump with the encapsulation unit.

It may be found advantageous to add various agents (e.g. albumin, clacium alginate and the like) to the initial cell emulsion to assist in preserving the cells during subsequent processing steps.

It may also be found advantageous to add a surfactant (e.g. PLURONIC L62, from BASF Wyandotte) prior to centrifuging to assist in preventing the soft beads from coalescing during centrifugation. After separation, it is desirable to treat the encapsulated cell beads with an isotonic saline solution, with mixing, one or more times, to "harden" the membrane shell and prepare beads of appropriate quality and integrity. Then the viable cells are ready for preparation into appropriate dosage form, and administration to a body in an appropriate manner.

The invention is further illustrated in the following specific examples.

EXAMPLE 1

EUDRAGIT RL (Rohm Pharma Gmbh., Darmstadt, W. Germany), an acrylic acid ester/methacrylic acid ester copolymer containing a low content of quaternary ammonium groups was dissolved in a 75/25 (v/v) mixture of ethyl acetate and DMSO. 0.2 mL of this solution (27.4% w/v polymer was added, slowly, over a two minute period, to a well-stirred dispersion containing 0.4 mL of human whole blood or packed cells suspended in aqueous phosphate buffered saline (Red Cross Blood Bank, Toronto, Ontario) in 25 mL of mineral oil. Stirring was continued for a further 3 minutes.

5 mL of PBS (phosphate buffered saline) containing 15% DMSO (v/v) was added to the dispersion and the mixture was centrifuged at low speed to remove the mineral oil supernatant. The DMSO was removed gradually in subsequent 5 mL washes followed by centrifugation with PBS containing progressively lower concentrations of DMSO (10%, 5%, 0%, DMSO).

Three further washes with pure PBS, followed by centrifugation at low speed, were used to separate free or partially encapsulated cells from the microcapsules.

EXAMPLE 2

Microscopic examination was used to assess qualitatively the effectiveness of the encapsulation process Cell lysis was quantified by spectrophotometric measurement of cyanmethemoglobin at 540 nm. Average capsule diameter was approximately 150 μm. The cells, unchanged in colour, were encapsulated in clumps, but with the cell membrane distinctly separating individual cells. The cells were not uniformly distributed among the capsules, however. With each wash the mixture was separated into three fractions; micro-capsules containing cells, free cells and an aqueous supernatant containing some hemoglobin. The free cells which had been subject to the encapsulation conditions yet not encapsulated appeared intact microscopically (normal shape), took up oxygen freely, (turned bright pink when air was bubbled through an aliquot of resuspended cells) and lysed normally when placed in distilled water. In contrast, free cells after encapsulation using a pure DMSO solution of polymer were fixed, did not lyse in distilled water and had turned brown.

The estimated yield of encapsulated cells from whole blood was approximately 1-6% as determined by comparing the total amount of hemoglobin in the unencapsulated fractions (free cells and lysate) with the amount of hemoglobin in 12 drops of whole blood. Under the indicated experimental conditions, approximately 20% of the hemoglobin of the non-encapsulated cells was recovered as free hemoglobin during the aqueous washing steps. About 40–45% of this (i.e. 8–9% of the total) was recovered in the initial 15% DMSO/PBS wash; this represents the degree of cell lysis that occurred during both encapsulation and this initial wash step.

Encapsulated cells placed in distilled water lost hemoglobin slowly (overnight) to the surrounding fluid, indicating the low permeability of the EUDRAGIT capsules to proteins as large as hemoglobin. Spectrophotometric analysis of the distilled water supernatant indicated that the hemoglobin was not oxidized and that approximately 6% of the total cells were originally encapsulated, in agreement with the number estimated by hemoglobin balance for this batch of cells. Hemoglobin did not leak from encapsulated cells placed in PBS, indicating that the encapsulated cells were intact, but were not fixed, lysing normally in hypotonic solutions. Removing the polymer coating by placing the capsules that had been in PBS in pure DMSO produced a brown pellet of fixed cells but no such pellet was found with the capsules that had been in distilled water, further indicating the intact state of the encapsulated cells.

Unlike conventional coacervation methods in which a non-solvent is added to a suspension of cells or other material in a polymer/solvent continuous medium to precipitate the polymer around the discrete phase, this method appears to rely on the high partition coefficient of DMSO between water and mineral oil. The DMSO solubilized the polymer in the mineral oil. Because of the high partition coefficient, however, the DMSO was removed from the oil phase in the presence of the discrete aqueous phase. The removal of the solubilizing agent caused the polymer to precipitate at the water/oil interface. Accordingly the capsule was formed very rapidly (5 minutes), since the rate of capsule formation was limited by the rate of DMSO removal and not by the slower rate of coacervate formation. Other polar solvents (e.g. ethanol) were found to be appropriate for microcapsule formation but they were incompatible with the cells.

EXAMPLE 3

0.2 mL of washed packed red blood cells suspended in phosphate buffered saline was further dispersed in 5 mL of a 8% solution of EUDRAGIT RL in diethylphthalate. 4 mL of this mixture was dispersed in 20 mL of mineral oil to which 10 mL of corn oil was quickly added followed by stirring for 10 minutes. After capsules had formed, a further 10 mL of corn oil was added, removed by decantation and followed by washing with 30 mL of fresh corn oil and then 30 mL of mineral oil. The mineral oil phase was replaced with 10 mL PBS followed by centrifugation to yield hard, non-sticky, essentially spherical capsules.

EXAMPLE 4

0.05 mL of washed packed red blood cells suspended in 0.05 mL of 9% bovine serum albumin aqueous solution was dispersed in 0.4 mLs of a 10% solution of Eudragit RL in dimethyl phthalate also containing 10% albumin. This mixture was added dropwise through an unstirred layer of corn oil (10 mL) into an unstirred bath of 2% albumin in PBS solution (100 mL). After all the cells were added the mixture was stirred for 15 minutes to further harden the capsules and remove the solvent. The capsules were recovered by centrifugation and washed twice with 2% albumin PBS to yield a hard granular product.

Encapsulated, viable mammalian cells according to the present invention have many useful applications of potential importance. For example, encapsulation of hepatocytes results in a functioning "artificial liver" for the treatment of acute hepatic coma or for drug detoxification. Encapsulation of interferon producing cells (e.g., human leukocytes, fibroblasts or lymphocytes) may facilitate the large scale production of interferon by increasing the surface-to-volume ratio of the culture, by increasing the stability of the cell and by simplifying the scale-up of the production process.

I claim:

1. A process for preparing micro-encapsulated viable mammalian cells for introduction to host, living mammalian tissue, which comprises:
   (a) preparing an aqueous suspension of said viable mammalian cells;
   (b) dispersing the aqueous suspension of cells in a relatively high molecular weight, hydrophobic, non-toxic, non-cell-penetrating liquid and agitating the dispersion to form an emulsion having a discontinuous aqueous phase comprising droplets containing small numbers of said viable cells;
   (c) adding to the emulsion so formed a solution of a biocompatible, water-insoluble polymer in a polar, non-toxic liquid solvent for said polymer;
   (d) precipitating the polymer at the interface of the aqueous, cell-containing droplets and the hydrophobic phase so as to encapsulate some at least of the cells in said droplets with a membrane of said polymer which will allow passage of cell substrates and secretions, but will prevent the passage of larger molecules; and
   (e) separating the bulk of the hydrophobic medium from the encapsulated cellular material.

2. The process of claim 1 including the further step of treating the encapsulated cellular material with saline to effect hardening of the polymeric membrane.

3. The process of claim 1 wherein said separation of the hydrophobic medium from encapsulated cellular material is effected by centrifugation in the presence of surfactant, to retard coalescence of the beads of encapsulated cellular material.

4. The process of claim 1 wherein the hydrophobic liquid is polypropylene glycol or mineral oil.

5. The process of claim 4 wherein the polymer is a copolymer of acrylic acid ester and methacrylic acid ester with a low content of quaternary ammonium groups.

6. The process of claim 5 wherein the polymer is in solution in dimethyl sulphoxide.

7. The process of claim 1 wherein polymer precipitation at the aqueous phase-hydrophobic phase interface is effected by slow addition to the mixture of a non-solvent for said polymer.

8. A process for preparing micro-encapsulated viable mammalian cells for introduction into hose, living mammalian tissue, which comprises:
   (a) preparing an aqueous suspension of said viable mammalian cells;
   (b) adding said aqueous suspension of viable cells to a solution of a biocompatible, water-insoluble polymer in a polar, non-toxic water remissible liquid solvent having molecular weight of at least 150, and forming a suspension having aqueous droplets containing said viable cells dispersed in a hydrophobic liquid medium;
   (c) adding to said suspension a non-solvent for the polymer to cause precipitation of the polymer at the interface of the aqueous, cell-containing droplets and the hydrophobic phase, so as to encapsulate some at least of the cells in said droplets with a membrane of said polymer which will allow passage of cell substrates and secretions, but will prevent the passage of larger molecules; and
   (d) separating the bulk of the hydrophobic medium from the encapsulated cellular material.

9. The process of claim 8 wherein the polymer is a copolymer of acrylic acid ester and methacrylic acid ester with a low content of quaternary ammonium groups, the polymer solvent is diethylphthalate, dimethylphthalate or dibutylphthalate, and the polymer non-solvent is corn oil.

10. The process of claim 8 wherein the polymer membrane is treated with albumin after precipitation thereof.

* * * * *